(12) United States Patent
Miles et al.

(10) Patent No.: US 6,602,907 B1
(45) Date of Patent: Aug. 5, 2003

(54) TREATMENT OF BREAST CANCER

(75) Inventors: Howard Miles, Winter Springs, FL (US); Solodnikov Sergey Yurjevich, Perm (RU); Krasnykh Olga Petrovna, Perm (RU); Pimenova Elena Valentinovna, Perm (RU); Elena A. Goun, Stanford, CA (US)

(73) Assignee: University of Central Florida, Orlando, FL (US)

( * ) Notice: Subject to any disclaimer, the term of this patent is extended or adjusted under 35 U.S.C. 154(b) by 17 days.

(21) Appl. No.: 10/164,541

(22) Filed: Jun. 7, 2002

Related U.S. Application Data

(60) Provisional application No. 60/296,823, filed on Jun. 8, 2001.

(51) Int. Cl.[7] .............................................. A61K 31/277
(52) U.S. Cl. ........................ 514/523; 514/557; 560/19; 562/459
(58) Field of Search ................................ 514/523, 557; 562/459; 560/19

(56) References Cited

U.S. PATENT DOCUMENTS

| | | | | |
|---|---|---|---|---|
| 5,308,852 A | * | 5/1994 | Girard et al. | 514/336 |
| 5,334,612 A | | 8/1994 | Kalden | 514/440 |
| 5,580,896 A | * | 12/1996 | Horwell et al. | 514/419 |
| 6,048,896 A | | 4/2000 | Giordani | 514/545 |
| 6,066,670 A | | 5/2000 | Brown | 514/557 |
| 6,083,985 A | * | 7/2000 | Yonemoto et al. | 514/568 |
| 6,121,450 A | | 9/2000 | Jones | 546/81 |
| 6,180,651 B1 | | 1/2001 | Nicolai | 514/336 |
| 6,232,312 B1 | | 5/2001 | Pamukcu | 514/237.5 |

* cited by examiner

*Primary Examiner*—Joseph K. McKane
*Assistant Examiner*—Robert Shiao
(74) *Attorney, Agent, or Firm*—Brian S. Steinberger; Roland A. Dexter; Law Offices of Brian S. Steinberger, P.A.

(57) ABSTRACT

Compounds of the class of 4-oxo-butenoic acid derivatives are disclosed along with the surprising use property of these compounds as a anti-tumor agents in humans against breast carcinoma, which include: 2-(N'-Fluoren-9-ylidene-hydrazino)-5,5-dimethyl-4-oxo-hex-2-enoic acid methyl ester (0F-06), 1-(2,4-Dimethyl-phenyl)-2,4-dihydroxy-3-(4-methyl-benzoyl)-5-oxo-2,5-dihydro-1H-pyrrole-2-carboxylic acid methyl ester (1F-07), 4-(4-Methoxy-phenyl)-2,4-dioxo-3-(phenyl-hydrazono)-butyric acid (3F-10), 4-(4-Chloro-phenyl)-2,4-dioxo-3-(phenyl-hydrazono)-butyric acid ethyl ester (3F-11), 2-Hydroxy-4-oxo-4-(2,3,5,6-tetrafluoro-4-methoxy-phenyl)-but-2-enoic acid (3F-15), and 4,4-Dihydroxy-5-(4-methyl-benzoyl)-2-phenyl-2,4-dihydro-pyrazol-3-one (3F-16) as well as some novel derivatives of these compounds claimed (see Table 2). The invention also encompasses a class of the compounds with the novel property of anti-tumor activity against human breast cancer, which includes the following compounds 4-(4-Ethoxy-phenyl)-2-(N'-fluoren-9-ylidene-hydrazino)-2-hydroxy-4-oxo-butyric acid methyl ester (0F-13); 2-{N'-[1-(4-Chloro-phenyl)-ethylidene]-hydrazino}-4-oxo-4-phenyl-but-2-enoic acid methyl ester (0F-20); 2-(N'-Fluoren-9-ylidene-hydrazino)-4-oxo-4-phenyl-but-2-enoic acid methyl ester (1F-04); and 4-Chloro-4-(4-ethoxy-phenyl)-2-(fluoren-9-ylidene-hydrazono)-but-3-enoic acid methyl ester (3F-19).

3 Claims, 2 Drawing Sheets

TREATMENT OF BREAST CANCER

This application claims benefit of Ser. No. 60/296,823 filed Jun. 8, 2001.

FIELD OF THE INVENTION

This invention relates to novel 4-oxo-butenoic acid derivatives and to the use of these compounds and related compounds with novel biological activity in humans as therapeutic means for the prevention and treatment of the human breast cancer and claims the benefit of priority of U.S. Provisional Application Serial No. 60/296,823 filed Jun. 8, 2001.

BACKGROUND OF THE INVENTION

Cancer is a global killer of humans with breast cancer among the leaders of killing humans yearly. Breast cancer is the primary killer of women. One in eight American women will develop breast cancer in her lifetime. In 2001, an estimated 192,700 women in the U.S. will be diagnosed with invasive breast cancer and 42,600 with in situ (tumors contained in the milk ducts). An estimated 40,000 will die from the disease.

An estimated 3 million women in the U.S. today are living with breast cancer of which 2 million have been diagnosed with the disease and I million have the disease but do not yet know it.

The incidence of breast cancer in the U.S. has more than doubled in the past 30 years. In 1964, the lifetime risk was 1 in 20. Today it's 1 in 8. Breast cancer is the most commonly diagnosed cancer in women in both America and worldwide. Breast cancer rates are the highest in industrialized countries. It is estimated that 1.2 million new diagnoses and 500,000 deaths from breast cancer will occur worldwide this year. Further, it appears that breast cancer is the leading cause of death for American women of ages 25 to 55 years.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. {Porter-Jordan and Lippman, Breast Cancer 8:73–100 (1994)}. However, the use of established markers often leads to a result that is difficult to interpret, and the high mortality observed in breast cancer patients indicates that improvements are needed in the treatment, diagnosis and prevention of the disease.

Accordingly, there is a need for improved methods for chemotherapy for breast cancer. The present invention fulfills this need and further provides other related advantages.

The U.S. patent literature has many disclosures of oxobutenoic (crotonic) acid derivatives:

Pamukci (U.S. Pat. No. 6,232,312) describes crotonic acid derivatives (column 22, lines 43–58) for the treatment of colonic polyps;

Jones et al (U.S. Pat. No. 6,121,450) discloses crotonic acid derivatives (column 8, tine 34; column 78, line 24 and at example 34 as steroid modifiers in treating breast cancer (column 1, lines 55–58);

Kalden, et al (U.S. Pat. No. 5,334,612) discloses compounds said to be useful for treating AIDS including derivatives of carboxylic acid (column 9, line 31) and pyrrolidine (column 7, line 24);

Brown (U.S. Pat. No. 6,066,670) describes an anti-viral admixture containing crotonic acid for treating tumors (see Abstract);

Horwell, et al (U.S. Pat. No. 5,580,896) discloses many 4-oxo-2-butenoic acid derivatives (column 13, lines 21–59; also in columns 15+, examples 25,26,32,34,40, 43–46,77–79, 97,99,103,106,), which are useful for inhibiting colorectal cancer, i.e., colon cancer (Abstract); and, Giordani, et al (U.S. Pat. No. 5,580,890) discloses 4-oxo-2-butenoic acid derivatives said to be useful for treatment of AIDS (column 1, line 8 and column 2, line 61; and, Yonemeto, et al (U.S. Pat. No. 6,083,985) recites a number of anti-tumor or anti-AIDS agents that include butenoic acid derivatives.

The U.S. patent literature has many disclosures of butanoic acid derivatives including:

Nicolai, et al (U.S. Pat. No. 6,180,651) discloses many anti-inflammatory and analgesic compounds, including adenocarcinoma (column 1, line 55), which includes heterocyclic alcohol-esters (column 11, lines 1–16) and butanoic acid derivatives (many Examples including 47 through 162);

Girard, et al (U.S. Pat. No. 5,308,852) discloses many compounds including butanoic acid derivatives (see Methods B and C of schemes II and III) which compounds which are said to inhibit tumor metastasis (column 7, line 56 and column 8, line 4); and, Frechette (U.S. Pat. No. 5,696,117), Frechette(U.S. Pat. No. 5,854,242) and Frechette (U.S. Pat. No. 5,707,990) describe 148 benzoxazine and pyrido-oxazine heterocyclics as anti-bacterial compounds.

It appears from the foregoing that the derivatives of 4-oxo-butanoic acid of interest are not disclosed and thus there is no report of their activity against human breast cancer.

Consequently, there is a need for an anti-cancer drug for humans that mitigates the above mentioned disadvantages of current drug therapy and effectiveness against human breast cancer.

SUMMARY OF THE INVENTION

The first objective of the present invention is to provide a drug effective for treatment of human breast cancer.

Another object of this invention is to provide novel 4-oxo-butenoic acid derivatives.

A further object of this invention is to provide 4-oxo-butenoic acid derivatives with novel activity against human breast cancer.

A preferred embodiment of the invention encompasses a class of compounds having the property of anti-tumor activity against human breast cancer comprising the novel structures of 4-oxo-butenoic derivatives and more specifically those derivatives: 2-(N'-Fluoren-9-ylidene-hydrazino)-5,5-dimethyl-4-oxo-hex-2-enoic acid methyl ester (0F-06); 1-(2, 4-Dimethyl-phenyl)-2,4-dihydroxy-3-(4-methyl-benzoyl)-5-oxo-2,5-dihydro-1H-pyrrole-2-carboxylic acid methyl ester (1F-07); 4-(4-Methoxy-phenyl)-2,4-dioxo-3-(phenyl-hydrazono)-butyric acid (3F-10); 4-(4-Chloro-phenyl)-2,4-dioxo-3-(phenyl-hydrazono)-butyric acid ethyl ester (3F-11); 2-Hydroxy-4-oxo-4-(2,3,5,6-tetrafluoro-4-methoxy-phenyl)-but-2-enoic acid (3F-15); and 4,4-Dihydroxy-5-(4-methyl-benzoyl)-2-phenyl-2,4-dihydro-pyrazol-3-one (3F-16) as well as novel derivatives of these compounds (see Table 2).

The use of the following compounds for humans as therapeutic means for the eradication of human breast cancer further encompasses the following: 4-(4-Ethoxy-phenyl)-2-(N'-fluoren-9-ylidene-hydrazino)-2-hydroxy-4-oxo-butyric acid methyl ester (OF-13); 2-{N'-[1-(4-Chloro-phenyl)-ethylidene]-hydrazino}-4-oxo-4-phenyl-but-2-enoic acid methyl ester (OF-20); 2-(N'-Fluoren-9-ylidene-hydrazino)-4-oxo-4-phenyl-but-2-enoic acid methyl ester (1F-04); and 4-Chloro-4-(4-ethoxy-phenyl)-2-(fluoren-9-ylidene-hydrazono)-but-3-enoic acid methyl ester (3F-19).

Further objects and advantages of this invention will be apparent from the following detailed description of presently preferred embodiments, which are illustrated structurally in the accompanying drawings.

DESCRIPTION OF THE PREFERRED EMBODIMENTS

Before explaining the disclosed embodiments of the present invention in detail, it is to be understood that the invention is not limited in its application to the details of the particular arrangement shown since the invention is capable of other embodiments. Also, the terminology used herein is for the purpose of description and not of limitation.

As earlier recited this application has been filed in order to disclose: new 4-oxo-butenoic acids that have been found to have high activity against human breast cancer and low toxicity in animals.

Figure 1:
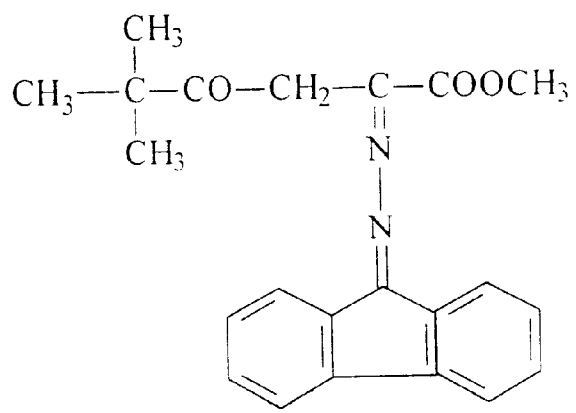
FIG. 1 illustrates structurally a chemical compound designated as OF-06.
Figure 2:
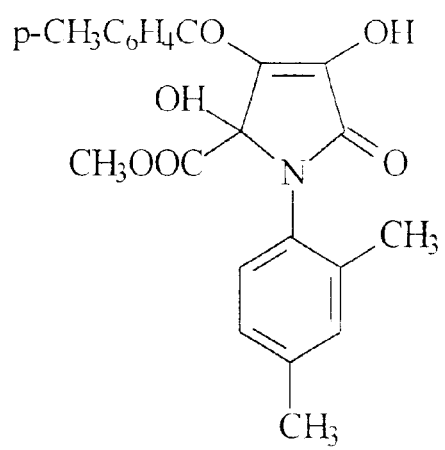
FIG. 2 illustrates structurally a chemical compound designated as 1F-07.
Figure 3:
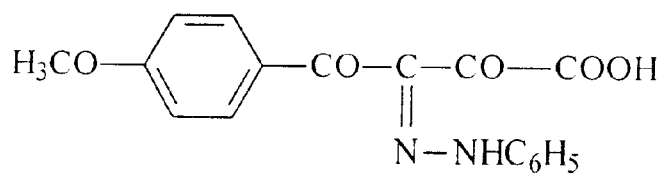
FIG. 3 illustrates structurally a chemical compound designated as 3F-10
Figure 4:
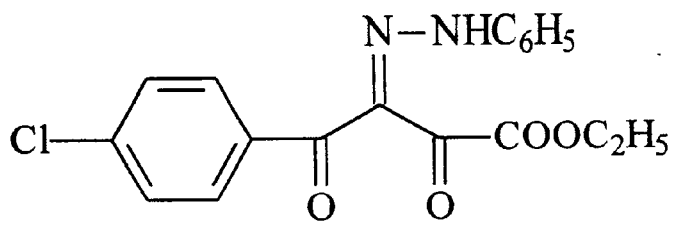
FIG. 4 illustrates structurally a chemical compound designated as 3F-11
Figure 5:
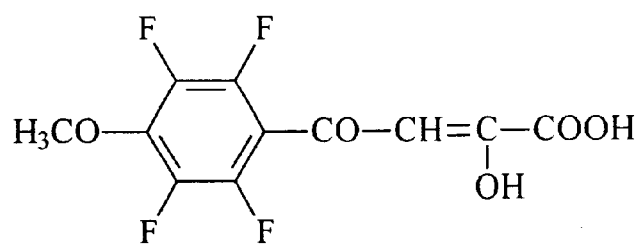
FIG. 5 illustrates structurally a chemical compound designated as 3F-15
Figure 6:
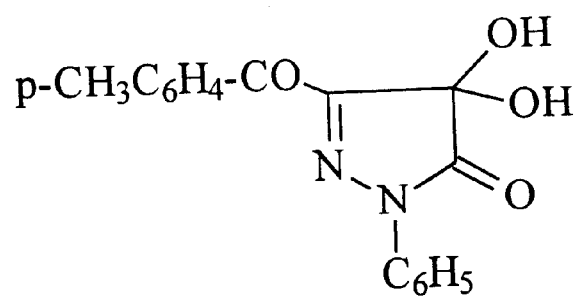
FIG. 6 illustrates structurally a chemical compound designated as 3F-16

More specifically this application is for the novel anti-tumor compounds OF-06, 1F-07, 3F-10, 3F-11, 3F-15 and 3F-16 which have been structurally shown in FIGS. 1–6, respectively, as well as novel derivatives of these compounds claimed (see Table2) and the activity against human breast cancer of compounds OF-13, OF-20, 1F-04, and 3F-19 also as shown in Table 1 along with anti-tumor activity and toxicity.

To facilitate a full understanding of the invention:

the compound designated as OF-06 is 2-(N'-Fluoren-9-ylidene-hydrazino)-5,5-dimethyl-4-oxo-hex-2-enoic acid methyl ester;

the compound designated as 1F-07 is 1-(2,4-Dimethyl-phenyl)-2,4-dihydroxy-3-(4-methyl-benzoyl)-5-oxo-2,5-dihydro-1H-pyrrole-2-carboxylic acid methyl ester;

the compound designated as 3F-10 is 4-(4-Methoxy-phenyl)-2,4-dioxo-3-(phenyl-hydrazono)-butyric acid the compound designated as 3F-11 is 4-(4-Chloro-phenyl)-2,4-dioxo-3-(phenyl-hydrazono)-butyric acid ethyl ester;

the compound designated as 3F-15 is 2-Hydroxy-4-oxo-4-(2,3,5,6-tetrafluoro-4-methoxy-phenyl)-but-2-enoic acid and, the compound designated as 3F-16 is 4,4-Dihydroxy-5-(4-methyl-benzoyl)-2-phenyl-2,4-dihydro-pyrazol-3-one.

These compounds have very.high activity against human breast cancer and a very low toxicity as Lethal Dose 50 ($LD_{50}$) in animals. The percent activity and animal toxicity for each compound is as follows:

OF-06 (100% against human breast carcinoma and $LD_{50}>3000$ mg/kg);

1F-07 (100% against human breast carcinoma and $LD_{50}>500$ mg/kg);

3F-10 (100% against human breast carcinoma and $LD_{50}$, <750 mg/kg);

3F-11 (100% against human breast carcinoma and $LD_{50}>2000$ mg/kg);

3F-15 (100% against human breast carcinoma and $LD_{50}>200$ mg/kg); and, 3F-16 (100% against human breast carcinoma and $LD_5>500$ mg/kg)

PREPARATION OF (OF-06).

EXAMPLE 1

The preparation of 2-(N'-Fluoren-9-ylidene-hydrazino)-5,5-dimethyl-4-oxo-hex-2-enoic acid methyl ester (OF-06). A solution of 5.0 g (0.02 moles) of 2-hydroxy-5,5-dimethyl-4-oxo-hex-2-enoic acid methyl ester (1) (synthesis was previously published by E. Royals. *J.Am.Chem.Soc.*, 1945, 67, 1508) and 3.88 g (0.02 moles) of fluoren-9-ylidene-hydrazine (2) in 80 mL of absolute toluene was refluxed for 3 hr 30 min with a Dean-Stark trap (control for the end of the reaction was carried by TLC). The solution was cooled and the precipitate was filtered and recrystallized from absolute benzene-hexane (1:1) to give 3.4 g (68% yield) of yellow crystals, mp 135–137° C.

Solubility: highly soluble in DMSO, DMFA, dichloroethane, acetonitrile, slightly soluble in ethanol, tetrachloromethane, insoluble in hexane and water.

The synthesis of OF-06 is an example of well known amination/dehydration reactions.

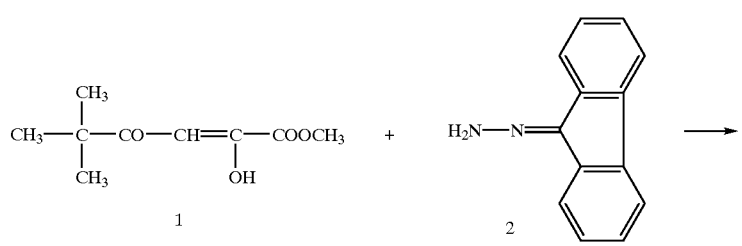

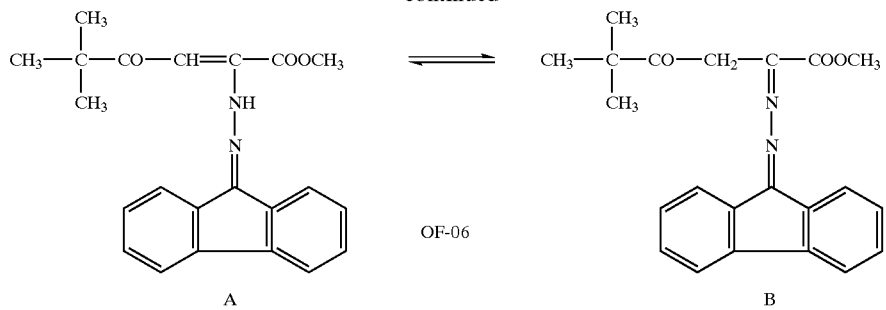

A            B

PREPARATION OF (1F-07)

EXAMPLE 2

The preparation of 1-(2,4-Dimethyl-phenyl)-2,4-dihydroxy-3-(4-methyl-benzoyl)-5-oxo-2,5-dihydro-1H-pyrrole-2-carboxylic acid methyl ester (1F-07). To a solution of 1.65 g (0.0051 moles) of 2-(2,4-diinethyl-phenylamino)-4-oxo-4-p-tolyl-but-2-enoic acid methyl ester (1) in 20 mL of anhydrous chloroform was added 0.68 g (0.0054 moles) oxalyl chloride. After refluxing for 30 min, 10 mL of anhydrous hexane was added and 15 ml of solvent was distilled out. The remainder of the solvent was evaporated by keeping the flask open for 12 hr. The resulting precipitate was filtered and recrystallized from dichloroethane—tetrachlorometane (1:2) to give 1.25 g (62%) of compound 1F-7 in the form of white crystals, mp 133–135° C. (decomp.)

Solubility: highly soluble in DMSO, acetonitrile, slightly soluble in dichloroethane, benzene, insoluble in hexane tetrachloromethane and water.

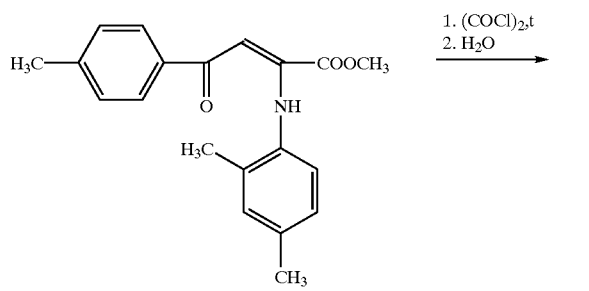

1F-7

PREPARATION OF (3F-10)

EXAMPLE 3

The preparation of 4-(4-Methoxy-phenyl)-2,4-dioxo-3-(phenyl-hydrazono)-butyric acid (3F-10). To a hot stirred solution of 0.075 moles of 2-Hydroxy-4-(4-methoxy-phenyl)-4-oxo-but-2-enoic acid in 300 ml of dioxane small potions of an aqueous solution prepared from 0.075 moles of aniline, 0.92 moles of sodium nitrate and 19 ml of concentrated HCl in 90 ml of water (DI) was added. During cooling 11.4 g of sodium acetate was added and the reaction was kept at the r.t. for 24 hr. Then 2 L of water was added to the reaction mixture and the resulting precipitate was filtrated and recrystallized from 1:1 mixture of dimethyl chloride/ethyl acetate to give 15.93 g of yellow crystals (60% yield) with m.p. of 176–177 (decomp).

Solubility: highly soluble in DMSO, DMFA, slightly soluble in chloroform, dichloroethane; insoluble in hexanes.

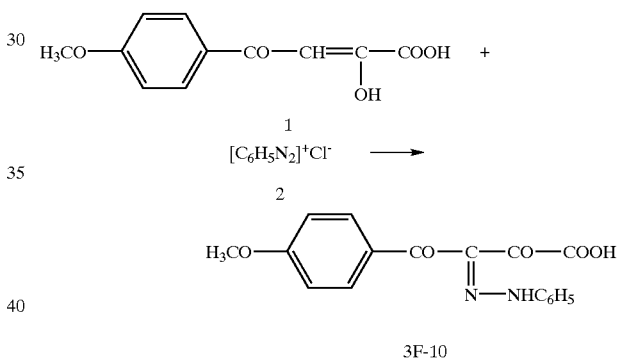

3F-10

PREPARATION OF (3F-11)

EXAMPLE 4

The preparation of 4-(4-Chloro-phenyl)-2,4-dioxo-3-(phenyl-hydrazono)-butyric acid ethyl ester (3F-11). A solution of 0.5 g (0.0016 moles) of 5-(4-Chloro-benzoyl)-2-phenyl-2H-pyrazole-3,4-dione (1) (synthesis was previously published by Pimenova, E. V; Andreichikov, Yu. S. (1992) *Zh. Org. Khim.* 28, 376–89). in 2 mL of anhydrous ethanol was refluxed for 1 hr. The resulting solution was cooled and the precipitate was filtered to give 0.48 g (85% yield) of yellow crystals with m.p. of 141–142° C. (decomp).

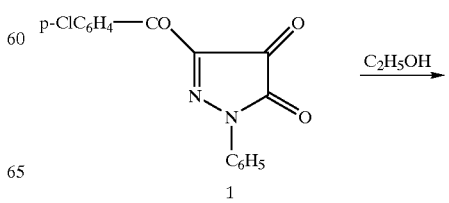

1

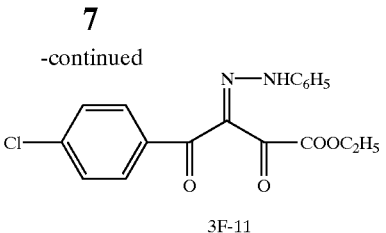

3F-11

PREPARATION OF (3F-15)

EXAMPLE 6

The preparation of 2-Hydroxy-4-oxo-4-(2,3,5,6-tetrafluoro-4-methoxy-phenyl)-but-2-enoic acid (3F-15). A solution of sodium methoxide was prepared from 0.46 g (20 mmol) of sodium and 30 mL of absolute methanol by adddding small portions to a mixture of 6.35 g (10 mmol) of I-pentafluorophenyl-ethanone 1 and 3.54 g (10 mmol) of dimethyl oxalate 2. After stirring the reaction for 24 hr at rt, 50 mL of 25% aqueous solution of HCl was added. The resulting mixture was extracted with ether (240 mL), washed by solution of brine and dried over anhydrous $Na_2SO_4$. The solvent was removed in vacuum and 10 mL of saturated solution of NaOH in ethanol was added with stirring. After 1 hr the reaction mixture was diluted with water and acidified with $H_2SO_4$ (10%) to obtain pH of 1–2. The resulting precipitate of 3F-15 was filtered and recrystallized from toluene to give 1.73 g (81% yield) in the form of white-yellow crystals, mp 155–156° C. (decomp.).

$C_6F_5$—CO—$CH_3$ + $(COOCH_3)_2$ → 1) $2CH_3ONa$ 2) HCl 3) $NaOH/C_2H_5OH$ 1    2

3F-15

PREPARATION OF (3F-16)

EXAMPLE 7

The preparation of 4,4-Dihydroxy-5-(4-methyl-benzoyl)-2-phenyl-2,4-dihydro-pyrazol-3-one (3F-16). A solution of 0.5 g (0.0017 moles) of 5-(4-Methyl-benzoyl)-2-phenyl-2H-pyrazole-3,4-dione (1) (synthesis was previously published by Pimenova, E. V; Andreichikov, Yu. S. (1992) *Zh. Org. Khim.* 28, 376–89), and 5 mL of water (DI) was kept at the rt until the solution became colorless and precipitate was formed. The precipitate was filtered and recrystallized from dichloroethane-water (10:1) to give 0.45 g (85%) of yellow-brown crystals, mp 134–135° C.

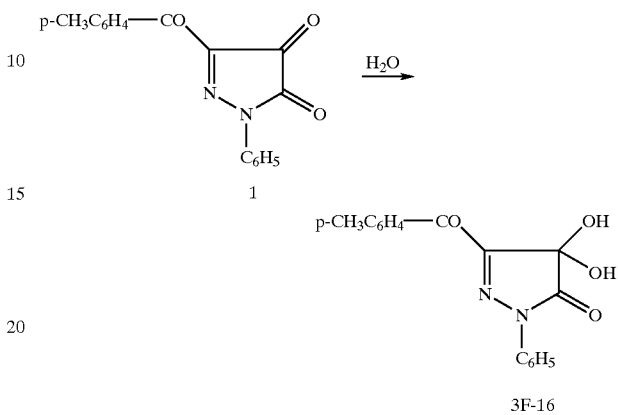

Solubility: highly soluble in DMSO, dioxane, insoluble in water.

PREPARATION OF (0F-13)

EXAMPLE 8

The preparation of 4-(4-Ethoxyphenyl)-2-(N'-fluoren-9-ylidene-hydrazino)-2-hydroxy-4-oxobutyric acid methyl ester-(0F-13). A solution of 5.0 g (0.02 moles) of methyl 4-p-ethoxyphenyl-2-hydroxy-4-oxo-2-butenoate (1) and 3.88 g (0.02 moles) of fluorene-9-ylidene-hydrazine (2) in 80 mL of absolute benzene and absolute toluene (1:1) was refluxed for 1 hr 30 min with a Dean-Stark trap (the end of the reaction was determined by TLC), cooled and the precipitate was filtered and recrystallized from benzene - diethyl ether - hexane mixture (1:3:2) to give 2.65 g (53% yield) of colorless crystals with mp 114–116° C.

Solubility: highly soluble in DMSO, DMFA, dichloroethane, acetonitrile, insoluble in hexane. The compound is not stable in solutions and decomposes quickly when the solution is heated or stored for a long time with the formation of 0F-12.

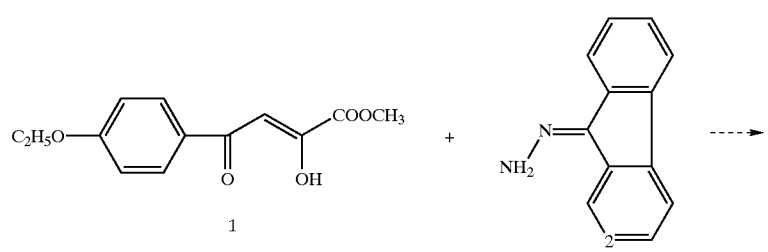

-continued

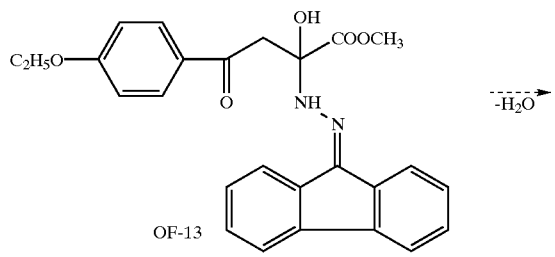

OF-13

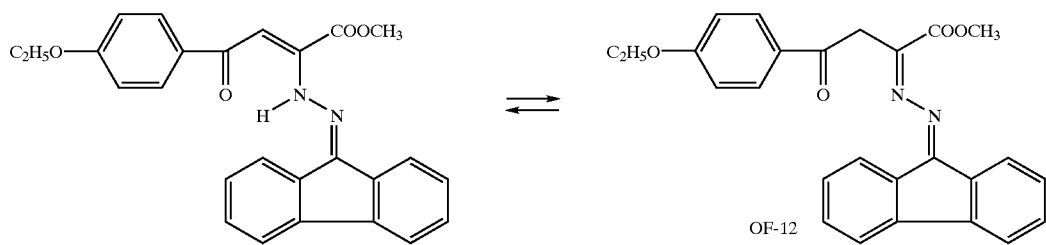

OF-12

It is seen from the above that (OF-13) is an intermediate product during the synthesis of (OF-12).

PREPARATION OF (3F-19)

EXAMPLE 9

The preparation of 4 Chloro 4 (4 ethoxy phenyl) 2 (fluoren 9 ylidene hydrazono) but 3 enoic acid methyl ester (3f-19) to the solution of 10 g (0.0026 moles of 4 (4 Ethoxy phenyl) 2 (N'fluoren 9 yliden hydrazine) 4-oxo-but-2-enoic acide methyl ester (OF-12) (synthesis was previously published by Konyukhova, N. A.; Krasnykh, O. P.; Aliev, Z. G.; Maslivets, A. N. *Cehmistry of Hetorcyclic Compounds* (New York, N.Y., United States) (Translation of Khimiya Geterotsiklicheskikh Soedineii) (2001), 37(6), 779–780) in 5 mL of anhydrous benzene 0.3935 g (0.0031 moles) oxalyl chloride was added. The reaction mixture was refluxed for 1 hour 40 min, cooled, precipitate was filtered and recrystallized from absolute benzene to give 0.62 g (54%) of yellow crystals, m.p. 163–163 (decom).

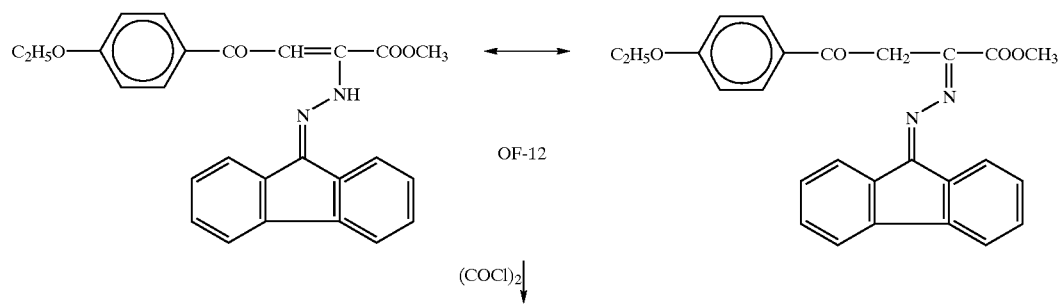

OF-12

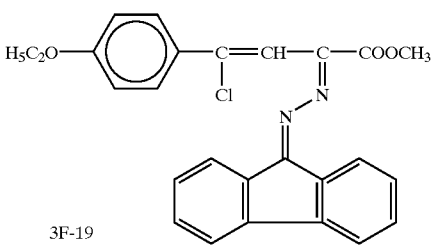

3F-19

TABLE 1

Some Compounds of the Invention

| # | Structure | Name | Activity (ATCC HTB123) | LD$_{50}$, mg/kg | Reference |
|---|---|---|---|---|---|
| OF-13 | 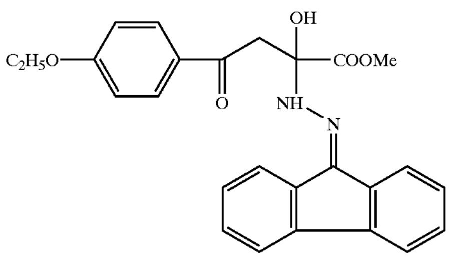 | 4-(4-Ethoxy-phenyl)-2-(N'-fluoren-9-ylidene-hydrazino)-2-hydroxy-4-oxo-butyric acid methyl ester | 100% | >1500 | Miles et. al. UCF-303A |
| OF-20 | 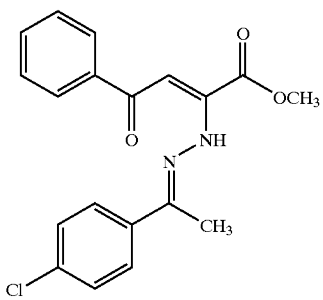 | 2-{N'-[1-(4-Chloro-phenyl)-ethylidene]-hydrazino}-4-oxo-4-phenyl-but-2-enoic acid methyl ester | 83% | >250 | Miles et. al. UCF-311C |
| 1F-04 | 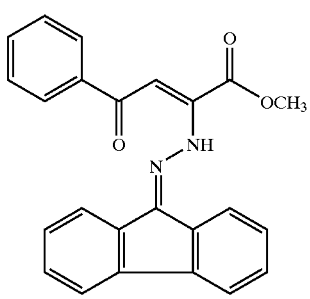 | 2-(N'-Fluoren-9-ylidene-hydrazino)-4-oxo-4-phenyl-but-2-enoic acid methyl ester | 93% | >1000 | Andrejchikov, Yurij S.; Maslivets, Andrej N.; Krasnykh, Olga P.; Aleksandrova, Galina A.; Vozhakova, Alla V. Russ. (1993), CODEN: RUXXE7 RU 2003655 C1 19931130 Application: RU 91-5013322 19910704. |
| 3F-19 | 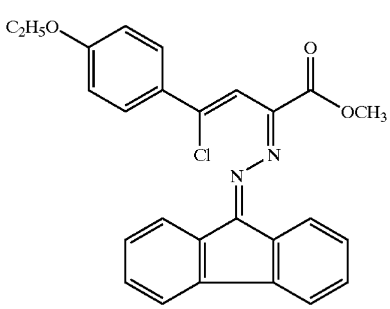 | 4-Chloro-4-(4-ethoxy-phenyl)-2-(fluoren-9-ylidene-hydrazono)-but-3-enoic acid methyl ester | 100% | >200 | Konyukhova, N. A.; Krasnykh, O. P.; Aliev, Z. G.; Maslivets, A. N. Chemistry of Heterocyclic Compounds (New York, NY, United States) (Translation of Khimiya Getero-tsiklicheskikh Soedinenii) (2001), 37(6), 779–780. |

TABLE 2

Derivatives of 3F-10 having potential anti-tumor activity

| # | Structure | Name |
|---|---|---|
| 1 | 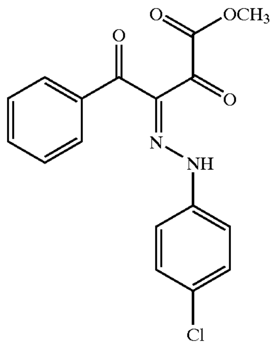 | 3-[(4-Chloro-phenyl)-hydrazono]-2,4-dioxo-4-phenyl-butyric acid methyl ester |
| 2 | 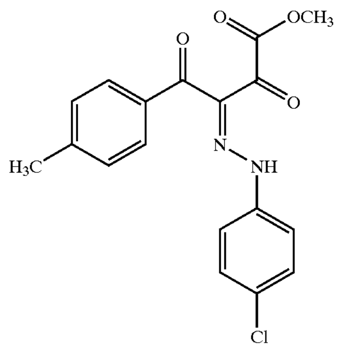 | 3-[(4-Chloro-phenyl)-hydrazono]-2,4-dioxo-4-p-tolyl-butyric acid methyl ester |
| 3 | 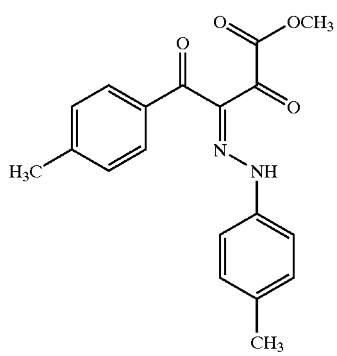 | 2,4-Dioxo-4-p-tolyl-3-(p-tolyl-hydrazono)-butyric acid methyl ester |
| 4 | 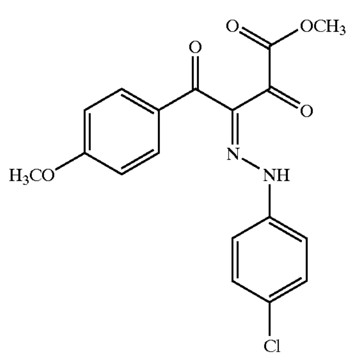 | 3-[(4-Chloro-phenyl)-hydrazono]-4-(4-methoxy-phenyl)-2,4-dioxo-butyric acid methyl ester |

TABLE 2-continued

Derivatives of 3F-10 having potential anti-tumor activity

| # | Structure | Name |
|---|---|---|
| 5 | 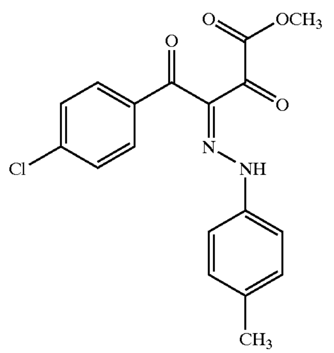 | 4-(4-Chloro-phenyl)-2,4-dioxo-3-(p-tolyl-hydrazono)-butyric acid methyl ester |
| 6 | 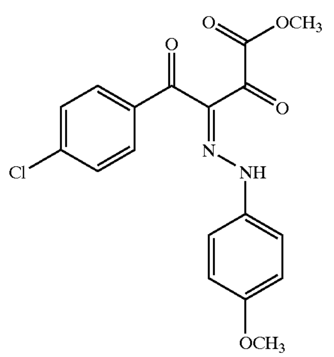 | 4-(4-Chloro-phenyl)-3-[(4-methoxy-phenyl)-hydrazono]-2,4-dioxo-butyric acid methyl ester |
| 7 | 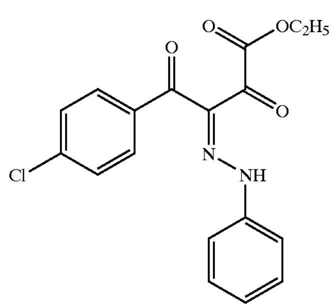 | 4-(4-Chloro-phenyl)-2,4-dioxo-3-(phenyl-hydrazono)-butyric acid ethyl ester |
| 8 | 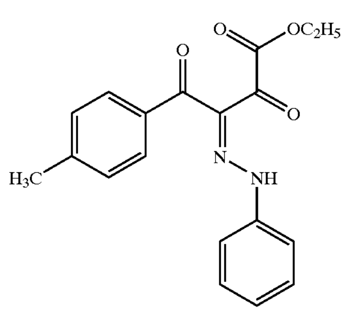 | 2,4-Dioxo-3-(phenyl-hydrazono)-4-p-tolyl-butyric acid ethyl ester |

TABLE 2-continued

Derivatives of 3F-10 having potential anti-tumor activity

| # | Structure | Name |
|---|---|---|
| 9 | 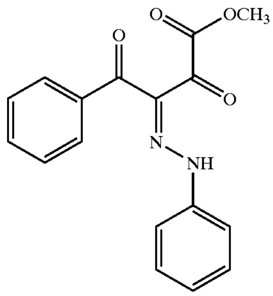 | 2,4-Dioxo-4-phenyl-3-(phenyl-hydrazono)-butyric acid methyl ester |
| 10 | 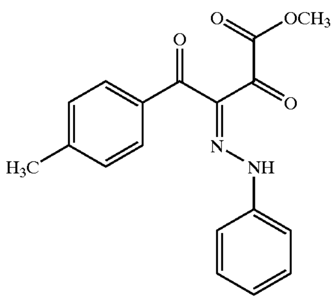 | 2,4-Dioxo-3-(phenyl-hydrazono)-4-p-tolyl-butyric acid methyl ester |
| 11 | 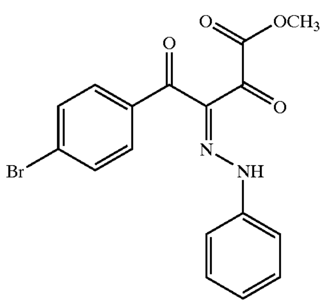 | 4-(4-Bromo-phenyl)-2,4-dioxo-3-(phenyl-hydrazono)-butyric acid methyl ester |
| 12 | 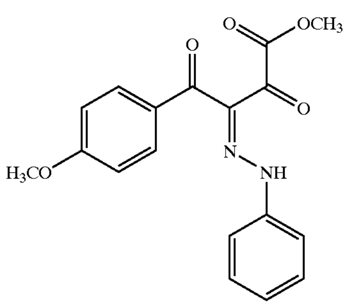 | 4-(4-Methoxy-phenyl)-2,4-dioxo-3-(phenyl-hydrazono)-butyric acid methyl ester |
| 13 | 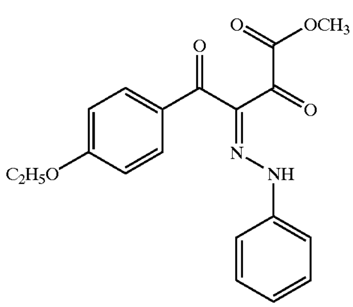 | 4-(4-Ethoxy-phenyl)-2,4-dioxo-3-(phenyl-hydrazono)-butyric acid methyl ester |

TABLE 2-continued

Derivatives of 3F-10 having potential anti-tumor activity

| # | Structure | Name |
|---|---|---|
| 14 | 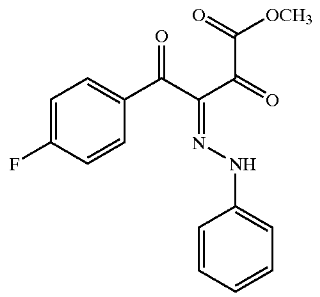 | 4-(4-Fluoro-phenyl)-2,4-dioxo-3-(phenyl-hydrazono)-butyric acid methyl ester |
| 15 | 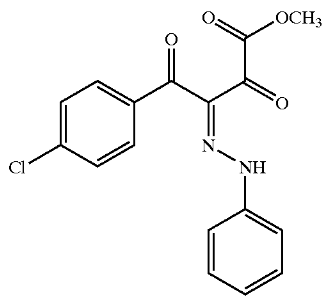 | 4-(4-Chloro-phenyl)-2,4-dioxo-3-(phenyl-hydrazono)-butyric acid methyl ester |
| 16 | 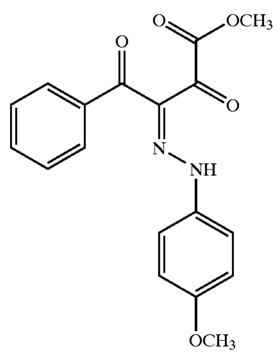 | 3-[(4-Methoxy-phenyl)-hydrazono]-2,4-dioxo-4-phenyl-butyric acid methyl ester |
| 17 | 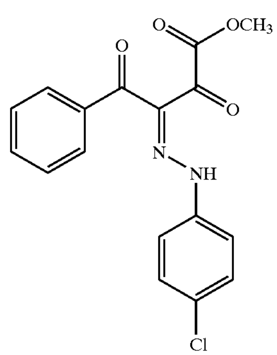 | 3-[(4-Chloro-phenyl)-hydrazono]-2,4-dioxo-4-phenyl-butyric acid methyl ester |

CYTOTOXICITY ASSAY

The activity in human breast cancer of the novel compounds (as earlier reported) was realized by the following procedure which determines the inhibitory effect of test samples on the growth of human breast cancer cells.

(ATCC HTB123) The HTB123 cells are grown in RPMI 1640 media +10% Fetal bovine serum +4.5g/L glucose +10 mM HEPES +1.0 mM sodium pyruvate +1% Antibiotic/Antimycotic for approximately 48 hours at 37° C./5% $CO_2$ in the presence of the test compound.

Growth/Non-Growth of the cells (e.g., cell density) is determined using Promega's MTS/PMS assay system. MTS (3-(4,5-dimethylthiazol-2-yl)-5-(3-carboxymethoxyphenyl)-2-(4-sulfophenyl)-2H-tetrazolium, inner salt) is an aqueous compound that is reduced to soluble formazan by the presence of NADH formed by dehydrogenases present within the HTB123 cells. The absorbance of the formazan can be measured at 490 nm and is directly proportional to the number of living cells present in the culture. PMS (Phenazine Methosulfate) is added an electron coupling reagent and greatly increases the rate of reduction.

To facilitate a full understanding of the procedure the following definitions are offered:

Test wells—wells containing test sample and Diluted HTB123 cells

Test values—absorbance of test wells

Blank wells—wells containing test sample and HTB 123 media (HHTB2-01S); used to obtain background absorbance due to test sample Blank values—absorbance of blank wells Negative Control—maximal cell growth; results of test samples will be expressed as a percent of the Negative Control Positive Control—known inhibitor of HTB 123 cells; used to validate assay system Matrix—solvent that the samples are prepared/diluted in Assay samples of similar origin and matrix (e.g., methanol extraction, methylene chloride extraction, water soluble samples, etc.) together on the same plate in order to reduce the number of steps performed per plate.

Blank values will be determined for each sample to account for any color contribution due to the sample itself. These blank wells must contain the same amount of sample plus HTB 123 media (no cells). After completion of MTS/PMS reaction blank values will be subtracted from the test value to obtain a net absorbance that will be used to calculate cell density.

All results are based upon a comparison to the Negative Control value of the plate. The Negative Control must contain the same amount of matrix (e.g., solvent) to offset any destructive effect the matrix may have on the growth of the HTB123 cells (allows for baseline values to be set).

For most samples, a HTB123 cell growth (diluted two to four-fold, depending upon the appearance of the inoculum*) of approximately 48 hours followed by and incubation of 3 hours with the MTS/PMS Reagent is optimal.

*Due to the nature of the HTB123 cells it is very difficult to obtain accurate cell densities. Continuation of the HTB123 cell line typically consists of the dilution of mature cells at two or three-fold into fresh media and growth at 37° C./5% $CO_2$ for two to three days.

In order to establish the accuracy of this assay a Positive Control consisting of 50 μM Methotrexate should not decrease the net absorbance to less than 90% of the Negative Control (HTB123 cells are somewhat resistant to methotrexate) is utilized.

ANIMAL TOXCITY BIOASSAY

Acute toxicity was studied on white mice of both sexes with weight ranging between 18–26 grams under intraperitoneal injection of 2% solution of tested compound in starch (the compound was dissolved in starch slime and injected) on the basis of 0.1 ml of solution per 10 g of the animal weight. Each dose was tested on the group of 6 animals that were observed during 14 days period. (This method was approved by the Pharmacology committee of Russian Ministry of Health and has been widely used since 1968.) Averaged lethal dose ($LD_{50}$) of the compound was computed using results of experiments on 5–7 groups of animals using method of Litchfield and Wilkinson. (Belenkii M. L. "Elements of quantative determination of the pharmacological effect," Leningrad, 1963, 71 pages).

USE OF THE INVENTION FOR TREATMENT OF HUMAN BREAST CANCER

The compounds of the invention, i.e. 4-oxo-butenoic acids derivatives and more specifically those novel derivatives: 2-(N'-Fluoren-9-ylidene-hydrazino)-5,5-dimethyl-4-oxo-hex-2-enoic acid methyl ester (0F-06); 1-(2,4-Dimethyl-phenyl)-2,4-dihydroxy-3-(4-methyl-benzoyl)-5-oxo-2,5-dihydro-1H-pyrrole-2-carboxylic acid methyl ester (1F-07); 4-(4-Methoxy-phenyl)-2,4-dioxo-3-(phenyl-hydrazono)-butyric acid (3F-10); 4-(4-Chloro-phenyl)-2,4-dioxo-3-(phenyl-hydrazono)-butyric acid ethyl ester (3F-11); 2-Hydroxy-4-oxo-4-(2,3,5,6-tetrafluoro-4-methoxy-phenyl)-but-2-enoic acid (3F-15) and, 4,4-Dihydroxy-5-(4-methyl-benzoyl)-2-phenyl-2,4-dihydro-pyrazol-3-one (3F-16), as well as all novel derivatives of these compounds claimed (see Table2), and the additional compounds of Table 1 with activity against human breast cancer which include the following compounds 4-(4-Ethoxy-phenyl)-2-(N'-fluoren-9-ylidene-hydrazino)-2-hydroxy-4-oxo-butyric acid methyl ester (0F-13); 2-{N'-[1-(4-Chloro-phenyl)-ethylidene]-hydrazino}-4-oxo-4-phenyl-but-2-enoic acid methyl ester (0F-20); 2-(N'-Fluoren-9-ylidene-hydrazino)-4-oxo-4-phenyl-but-2-enoic acid methyl ester (1F-04); and 4-Chloro-4-(4-ethoxy-phenyl)-2-(fluoren-9-ylidene-hydrazono)-but-3-enoic acid methyl ester (3F-19).

All the compounds are unique in the in vitro treatment of humans and can be used as therapeutic means for the eradication of tumors from the human breast in a pharmaceutical composition comprising a non-toxic effective amount of the referenced compound or a tautomeric form thereof or a pharmaceutically acceptable salt thereof or pharmaceutically acceptable solvate thereof, and a pharmaceutically acceptable carrier thereof.

For administration to man in the curative or prophylactic treatment of human breast cancer in vitro dosages of compounds of the invention will generally be in the range of from 5 to 500 mg daily for an average adult patient (70 kg). Thus for a typical adult patient, individual tablets or capsules contain from 2–500 mg of active compound, in a suitable pharmaceutically acceptable vehicle or carrier, for administration in single or multiple doses, once or several times per day. Dosages for intraveneous, buccal or sublingual administration will typically be within the range of from 5–1000 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

The maximum human non-toxic one time administration dose for the compound(s) of the invention appears to range from 100 to 1500 mg.

For human use, the compounds of the invention can be administered alone or jointly, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution which may contain other substances, for example enough salts or glucose to make the solution isotonic with blood.

The invention thus provides a method for the treatment of breast carcinoma in a human mammal which comprises administering an effective, non-toxic, amount of a heterocyclic compound according to the invention or a tautomeric form thereof and/or a pharmaceutically acceptable salt thereof and/or a pharmaceutically acceptable solvate thereof to a breast carcinoma invaded human mammal in need thereof.

ADVANTAGES OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. The available drugs on the market have a variety of strong side effects, high cost and complicated synthesis. For example, Taxol is the most promising antitumor agent developed in the past three decades. It was approved by the FDA for the treatment of refractory ovarian cancer in December, 1992, and was introduced into the marketplace in January, 1993 by Bristol-Myers Squibb Company (BMS) operating under a Cooperative Research and Development Agreement (CRADA) with the National Cancer Institute (NCI). It was approved for the treatment of breast cancer in 1994, and is now in transition from second line to first line therapy. Worldwide sales of Taxol reached $1.2 billion in 1998. However, Preclinical development continued from 1977 until 1983, hampered by a number of obstacles, especially the formulation problem. Taxol is highly lipophilic and is insoluble in water. Finally, a vehicle consisting of a mixture of Cremophore EL (polyethoxylated caster oil), ethanol and saline was chosen, but its toxicity was a significant problem in preclinical studies. The main side effects of this drug were found to be congenital malformation in the fetus and reproductive disorders. The supply of Taxol was also a problem. To obtain Yew bark, the tree had to be killed. A large Pacific Yew two feet in diameter requires 200 years to grow and yields about five pounds of bark. In extractions by Polysciences, then the only extraction contractor, a 0.004% yield of Taxol was obtained. Furthermore, the Pacific Yew was a scarce understory tree, and its extinction and destruction of the old growth forests was threatened by the harvest. Few believed, because of the complexity of the molecule, that the problem of a commercial supply of Taxol could be solved by total synthesis. The first total synthesis was finally reported in 1994 by the Holton group. Although three total syntheses have been subsequently achieved by others, the Holton synthesis is the most efficient, but still requires over 40 steps from camphor and provides an overall yield of approximately 2%.

Taxol is perhaps best viewed as an exciting and valuable lead in cancer chemotherapy. Although Taxol has extended the life of many people, it is not a cure, and many patients develop resistance to it. Many tumor types show minimal or no response to Taxol, and there are solubility problems in drug delivery.

Accordingly, there is a need in the art for improved methods for therapy and diagnosis of breast cancer. The present invention fulfills these needs and further provides other related advantages. The animal toxicity bioassay data indicated that $LD_{50}$ dose for all of the compounds are in the range of 250–3000 mg/kg, which is much lower compare to some of the most promising agents against breast cancer. For example taxol intra-peritoneal $LD_{50}$ dose in mice using the same bioassay system is 218 mg/kg (JZKEDZ 6,1,1980), which is almost a number of magnitude higher then some of the claimed compounds. Such a low toxicity dose of the compounds claimed gives a strong potential for not to having such a serious side effects as the most potential drugs of the present time do. Secondly, more advantages from our invention are the cheapness and the simplicity of the synthesis of active compounds compare to the present drugs on the market. The synthesis of claimed compounds from commercially available reagents takes four to five synthetic steps with overall yield in the range of 60–85%. Versus for example taxol which takes minimum of 40 synthetic steps with only 2% overall yield, which increases the price of the compound dramatically.

Conclusion: Although the invented compounds have not yet been tested clinically, one can see from the Table 1 that all of them posses at least 10 times lower acute toxicity compare to the most promising antitumor agent developed in the past three decades, high activity values, ease of synthesis, and cheap cost. All these advantages provide a potential for the development of new drugs for the prevention or treatment of breast cancer.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A compound consisting of 2-(N'-Fluoren-9-ylidenehydrazino)-5,5-dimethyl-4-oxo-hex-2-enoic acid methyl ester.

2. A compound consisting of 2-Hydroxy-4-oxo-4-(2,3,5,6-tetrafluoro-4-methoxy-phenyl)-but-2-enoic acid.

3. A method of treating breast carcinoma in a human in need of such treatment comprising the steps of administering to said human, in a systemic, in vitro manner, an anti-tumor effective amount of a compound of claim 1 or claim 2 having the common property of anti-tumor activity against human breast cancer.

* * * * *